US00PP33378P2

(12) United States Plant Patent
Solano Ramirez

(10) Patent No.: US PP33,378 P2
(45) Date of Patent: Aug. 17, 2021

(54) ***PETUNIA* PLANT NAMED 'BALVOGED'**

(50) Latin Name: ***Petunia* x *hybrida***
Varietal Denomination: Balvoged

(71) Applicant: Ball Horticultural Company, West Chicago, IL (US)

(72) Inventor: Rolando Solano Ramirez, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/190,040

(22) Filed: Mar. 2, 2021

(51) Int. Cl.
*A01H 5/02* (2018.01)
*A01H 6/82* (2018.01)

(52) U.S. Cl.
USPC ..... Plt./356.12
CPC ..... *A01H 6/824* (2018.05)

(58) Field of Classification Search
USPC ..... Plt./356.12
CPC ..... A01H 5/02
See application file for complete search history.

*Primary Examiner* — Kent L Bell
(74) *Attorney, Agent, or Firm* — Andrey Charles

(57) ABSTRACT

A new and distinct cultivar of *Petunia* plant named 'Balvoged', characterized by its semi-double type, medium red-colored flowers, medium green-colored foliage, and moderately vigorous, mounded-spreading growth habit, is disclosed.

1 Drawing Sheet

Latin name of genus and species of plant claimed: *Petunia* x *hybrida*.

Variety denomination: 'Balvoged'.

BACKGROUND OF THE INVENTION

The present invention relates to a new and distinct cultivar of *Petunia* plant botanically known as *Petunia* x *hybrida* and hereinafter referred to by the cultivar name 'Balvoged'.

The new cultivar originated in a controlled breeding program in Guadalupe, Calif. during July 2017. The objective of the breeding program was the development of semi-double type *Petunia* cultivars that have a mounded-spreading growth habit.

The new *Petunia* cultivar is the result of cross-pollination. The female (seed) parent of the new cultivar is EASY WAVE Red 'PAS760704', not patented, characterized by its single-type, light red-colored, dark green-colored foliage, and moderately vigorous, mounded-spreading growth habit. The male (pollen) parent of the new cultivar is DOUBLE WAVE Pink 'Kirimaji Double Red', U.S. Plant Pat. No. 22,441, characterized by its double type, medium red-colored venation, medium green-colored foliage, and moderately vigorous, spreading and low mounded growth habit. The new cultivar was selected as a single flowering plant within the progeny of the above stated cross-pollination during January 2018 in a controlled environment in Guadalupe, Calif.

Asexual reproduction of the new cultivar by terminal stem cuttings since January 2018 in Guadalupe, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balvoged' as a new and distinct cultivar of *Petunia* plant:

1. Semi-double type, medium red-colored flowers;
2. Medium green-colored foliage; and
3. Moderately vigorous, mounded-spreading growth habit.

Plants of the new cultivar differ from plants of the female parent primarily in having semi-double type, medium red-colored flowers. Plants of the new cultivar differ from plants of the male parent primarily in having semi-double type flowers and a more mounded growth habit.

Of the many commercially available *Petunia* cultivars, the most similar in comparison to the new cultivar is DOUBLE WAVE Rose 'Kirimaji Double Rose', U.S. Plant Pat. No. 13,834. However, in comparison, plants of the new cultivar differ from plants of 'Kirimaji Double Rose' in at least the following characteristics:

1. Plants of the new cultivar have darker red-colored flowers than plants of 'Kirimaji Double Rose';
2. Plants of the new cultivar are taller and narrower than plants of 'Kirimaji Double Rose'; and
3. Plants of the new cultivar have larger diameter corollas than plants of 'Kirimaji Double Rose'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balvoged'. The approximately 14-week-old plants were grown in 6-inch pots for approximately 7 weeks in a greenhouse in West Chicago, Ill. Plants were given one pinch four weeks prior to transplant.

DETAILED BOTANICAL DESCRIPTION

Figure 1:
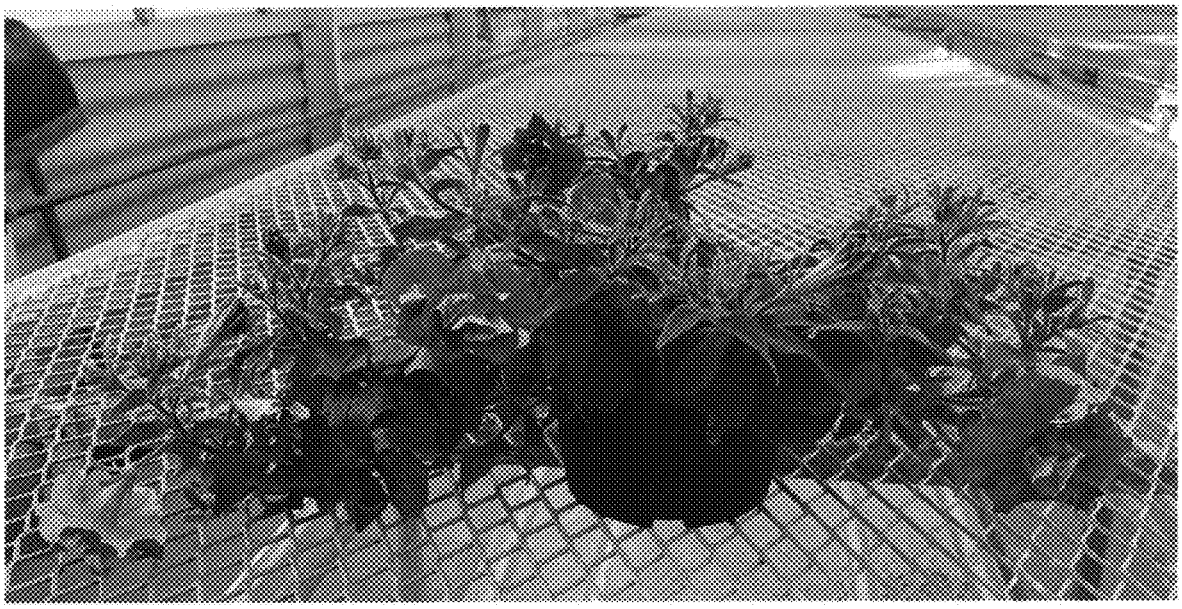
FIG. 1 illustrates a side view of the overall growth and flowering habit of 'Balvoged'.
Figure 2:
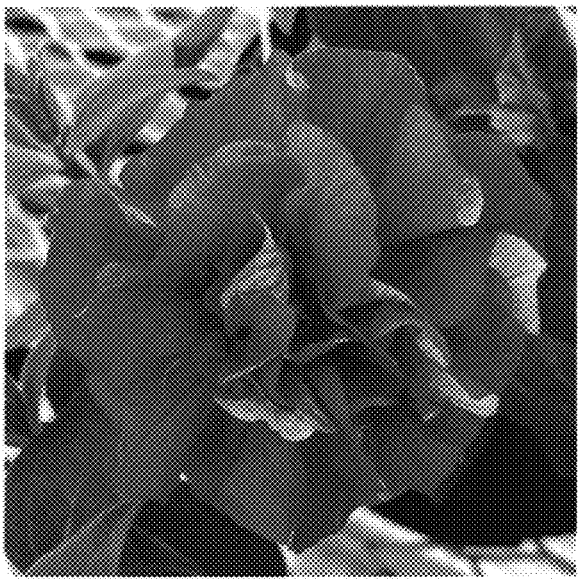
FIG. 2 illustrates a close-up view of an individual flower of 'Balvoged'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2020 under natural light conditions in West Chicago, Ill.

The following descriptions and measurements describe approximately 14-week-old plants produced from cuttings from stock plants and grown in a glass-covered greenhouse under conditions comparable to those used in commercial practice. The plants were grown in West Chicago, Ill. in 6-inch pots for approximately 7 weeks utilizing a soilless growth medium. Plants were given one pinch four weeks prior to transplant. Greenhouse temperatures were maintained at approximately 70° F. to 75° F. (21° C. to 24° C.) during the day and approximately 68° F. to 74° F. (20° C. to 23° C.) during the night. Supplemental lighting was used. Measurements and numerical values represent averages of typical plants.

Botanical classification: *Petunia* x *hybrida* 'Balvoged'.

Parentage:

*Female parent.*—EASY WAVE Red 'PAS760704', not patented.

*Male parent.*—DOUBLE WAVE Pink 'Kirimaji Double Red', U.S. Plant Pat. No. 22,441.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, mounded-spreading growth habit.

*Size.*—Height from soil level to top of plant plane: Approximately 19.0 cm. Width: Approximately 52.0 cm.

*Branching habit.*—Freely branching. Pinching enhances basal branching. Quantity of main branches per plant: Approximately 7.

*Branch.*—Strength: Moderate. Length: Approximately 27.0 cm. Diameter: Approximately 4.0 mm. Length of central internode: Approximately 3.0 cm. Texture: Densely glandular pubescent with a mixture of long and short hairs. Gland color: Colorless, transparent. Color of young stems: 144A. Color of mature stems: 146A.

Foliage description:

*General description.*—Quantity of leaves per main branch: Approximately 16. Fragrance: Slight. Form: Simple. Arrangement on flowering stem: Alternate.

*Leaves.*—Aspect: Acute angle to perpendicular to stem. Shape: Ovate. Margin: Entire. Apex: Acute. Base: Broadly attenuate to rounded. Venation pattern: Pinnate. Length of mature leaf: Approximately 5.5 cm. Width of mature leaf: Approximately 4.0 cm. Texture of upper and lower surfaces: Moderately glandular pubescent. Gland color: Colorless, transparent. Color of upper surface of young and mature foliage: 137A with venation of 146C to indistinguishable. Color of lower surface of young and mature foliage: Closest to 146B with venation of 146D to indistinguishable.

*Petiole.*—Length: Approximately 3.0 mm. Width: Approximately 4.0 mm. Texture: Densely glandular pubescent with a mixture of long and short hairs. Gland color: Colorless, transparent. Color: 146D.

Flowering description:

*Flowering habit.*—'Balvoged' is freely flowering under outdoor growing conditions with substantially continuous blooming from spring through autumn and year-round in greenhouse environment.

*Lastingness of individual flower on the plant.*—Approximately 10 to 12 days.

Flower description:

*General description.*—Type: Semi-double, hemispherical. Quantity per plant: Approximately 10. Fragrance: Slight.

*Bud.*—Rate of opening: Generally takes 3 to 5 days for bud to progress from first color to fully open flower. Quantity per plant: Approximately 8.

*Bud just before opening.*—Shape: Obovoid. Length: Approximately 3.2 cm. Diameter at apex: Approximately 1.4 cm. Diameter at base: Approximately 3.0 mm. Texture: Densely glandular pubescent. Gland color: Colorless, transparent. Color of petal portion: Closest to 182B with venation of 199A. Color of tube: Closest to 182C with venation of 199B.

*Corolla.*—Diameter: Approximately 7.3 cm.

*Petals.*—Quantity: Approximately 25 to 27, base fused to form a tube. Shape: Obovate. Appearance: Matte. Margin: Entire, ruffled. Apex: Cuspidate to rounded. Length from throat of outermost: Approximately 3.0 cm. Width of outermost: Approximately 3.2 cm. Length from throat of innermost: Approximately 1.6 cm. Width of innermost when flattened: Approximately 1.0 cm. Texture of upper surface: Glabrous. Texture of lower surface: Sparsely glandular pubescent. Gland color: Colorless, transparent. Color of upper surface when first and fully open: 45A to 45B with midveins of 46A. Color of lower surface when first and fully open: Closest to but lighter than 186D with midveins of closest to 199A with 146D.

*Corolla tube.*—Length: Approximately 3.0 cm. Diameter at distal end: Approximately 1.8 cm. Diameter at proximal end: Approximately 3.0 mm. Texture of inner surface: Glabrous. Texture of outer surface: Densely glandular pubescent. Gland color: Colorless, transparent. Color of inner surface: Closest to 47A and venation of 199D. Color of outer surface: Closest to but lighter than 186D with midveins of closest to 199C with 146D.

*Sepals.*—Quantity per flower: 5, fused at base. Shape: Linear. Margin: Entire. Apex: Broadly acute. Length: Approximately 2.0 cm. Width: Approximately 5.0 mm. Texture of upper and lower surfaces: Densely glandular pubescent. Gland color: Colorless, transparent. Color of upper surface: 137A. Color of lower surface: 138A with 145A at base.

*Peduncle.*—Strength: Strong, flexible. Aspect: Acute angle to stem. Length: Approximately 2.5 cm. Diameter: Approximately 2.5 mm. Texture: Densely pubescent with a mixture of long and short glandular hairs. Gland color: Colorless, transparent. Color: 146B.

*Reproductive organs.*—Androecium: Stamen quantity: Approximately 8 to 14, basifixed. Stamen length (if fully developed): Approximately 1.8 cm. Filament length of fixed portion: Approximately 5.0 mm to 1.7 cm. Filament color: NN155A tinted with 47D. Anther shape: Bilobed to irregular. Anther length: Approximately 1.0 mm. Anther color: 155A. Pollen amount: Moderate. Pollen color: 155A. Gynoecium: Pistil quantity: 1 per flower, vestigial.

Seed and fruit production: Neither seed nor fruit production has been observed.

Disease and pest resistance: Resistance to pathogens and pests common to *Petunia* has not been observed.

What is claimed is:

1. A new and distinct cultivar of *Petunia* plant named 'Balvoged', substantially as herein illustrated and described.

* * * * *